United States Patent [19]
Ploetz

[11] Patent Number: 5,878,104
[45] Date of Patent: Mar. 2, 1999

[54] METHOD FOR PRODUCING TOMOSYNTHESIS EXPOSURES EMPLOYING A REFERENCE OBJECT FORMED BY A REGION OF THE EXAMINATION SUBJECT

[75] Inventor: Josef Ploetz, Bensheim, Germany

[73] Assignee: Sirona Dental Systems GmbH & Co. KG, Bensheim, Germany

[21] Appl. No.: 857,947

[22] Filed: May 16, 1997

[30] Foreign Application Priority Data

May 17, 1996 [DE] Germany ................ 196 19 924.7

[51] Int. Cl.⁶ ...................................................... A61B 6/02
[52] U.S. Cl. ................... 378/22; 378/27; 378/205
[58] Field of Search ........................ 378/21, 22, 23, 378/24, 25, 26, 27, 205

[56] References Cited

U.S. PATENT DOCUMENTS

| | | | |
|---|---|---|---|
| 4,516,261 | 5/1985 | Harding et al. ................... | 382/131 |
| 5,237,998 | 8/1993 | Duret et al. ..................... | 128/665 |
| 5,394,457 | 2/1995 | Leibinger et al. ................. | 378/162 |
| 5,598,454 | 1/1997 | Franetzki et al. ................. | 378/206 |

FOREIGN PATENT DOCUMENTS

WO 93/2289  11/1993  WIPO .

*Primary Examiner*—David P. Porta
*Assistant Examiner*—David Vernon Bruce
*Attorney, Agent, or Firm*—Hill & Simpson

[57] ABSTRACT

In a method for producing a tomosynthesis exposure a reference object is used which is formed by a region of the examination subject. It is thus possible to determine the distance of the beam transmitter to the beam receiver and to the examination subject, the irradiation angle, and the direction of irradiation, on the basis of the signals that can be derived from the beam receiver during the transillumination of the reference object, without the reference object causing any disturbance in the region of the subject of examination.

10 Claims, 1 Drawing Sheet

METHOD FOR PRODUCING TOMOSYNTHESIS EXPOSURES EMPLOYING A REFERENCE OBJECT FORMED BY A REGION OF THE EXAMINATION SUBJECT

BACKGROUND OF THE INVENTION

1. Field of the Invention

The present invention is directed to a method for producing tomosynthesis exposures, and in particular to a method for producing tomosynthesis exposures of the type wherein a reference object is employed.

2. Description of the Prior Art

PCT application WO 93/22 893 discloses a method with which it is possible to reconstruct an exposure of an examination subject without the projection angle a and the geometrical arrangement of the radiation emitter and radiation receiver and the focal plane being known. According to this method, a reference object of radiation-absorbing material having a known size and a known spacing from the radiation receiver is provided in the region of the radiation receiver, this reference object being projected onto the radiation receiver in every individual projection. The geometrical arrangement and the two-dimensional projection angle a for each individual projection can be determined on the basis of the two-dimensional spatial imaging of the reference on the radiation receiver.

A holder for positioning a radiation emitter of an X-ray diagnostic apparatus for tomosynthesis is disclosed in German OS 44 14 689, corresponding to U. S. Pat. No. 5,598,454. A bracket is coupled to the holder, at which—as viewed in the radiation propagation direction—a spherical reference object is arranged in front of the examination subject and a radiation receiver is arranged behind the examination subject. The spacing of the radiation from the reference object and from the radiation receiver, as well as the angle a of a ray beam emitted by the radiation emitter relative to a reference axis of the holder mechanism, are prescribed by the holder. It is also known to arrange the radiation source so as to be adjustable in a housing to which a positioning means for the reference object and the radiation receiver can be coupled.

In such known tomosynthesis systems, because the reference object is disposed in front of the examination subject and is mounted on a bracket connected to the holder for the radiation receiver, the reference object can constitute a nuisance or an impediment in setting up the apparatus and conducting the examination.

SUMMARY OF THE INVENTION

An object of the present invention is to provide a method for producing a tomosynthesis exposure which employs a reference object, but wherein the necessity of using a separate reference object, remote from the examination subject, is avoided.

The above object is achieved in accordance with the principles of the present invention in a method for producing a tomosynthesis exposure wherein a reference object is employed that is formed by a region of the examination subject.

An advantage of the invention is that it is no longer necessary to use a separate reference object to produce a tomosynthesis exposure; rather, in the inventive method a reference object formed by a region of the examination subject is used. By means of the immediate, fixed relation of the reference object to the subject of examination, a particularly precise determination of the effective geometrical arrangement is also possible for each individual projection.

The reference object can be formed by a tooth filling, a crown, an implant or a metal part temporarily fastened to the examination subject or connected thereto. If the reference object is fastened immediately to the subject of examination via a mounting means, for example a cap or a ring, then, given known dimensions of the reference object, the size, i.e. the image scale, can be deduced immediately on the basis of the size relationships in the image.

The reference object can also be formed from a number of sub-objects. It is thereby possible to determine the geometrical arrangement of the reference object both relative to the beam receiver (detector) and relative to the source of radiation, and thus these do not need to be coupled either with one another or with the reference object. This also avoids any need for coupling either the radiation source or detector with the examination subject.

DESCRIPTION OF THE PREFERRED EMBODIMENTS

Figure 1:
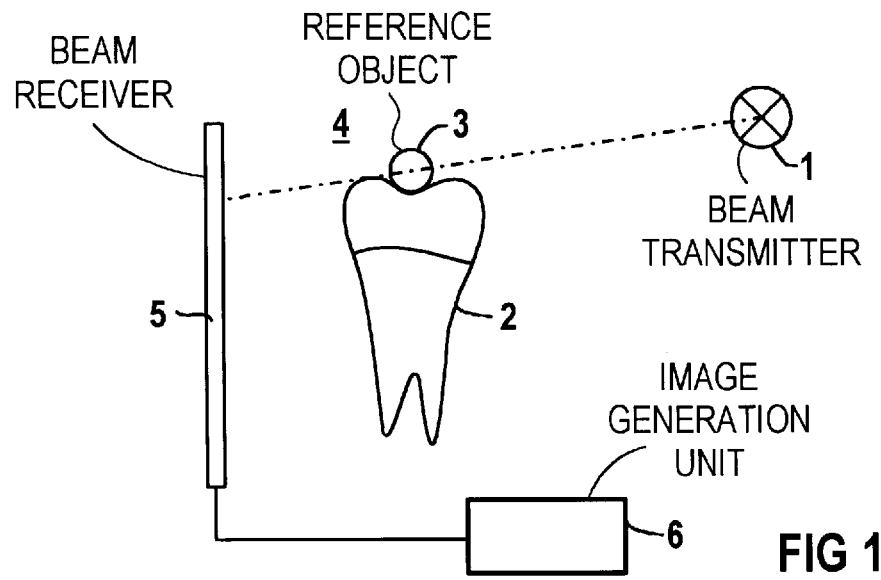
FIG. 1 shows an X-ray diagnostic apparatus operating with a reference object, according to a first embodiment of the inventive method.

The X-ray diagnostic apparatus shown in FIG. 1 has a beam transmitter 1, in particular a source of X-rays which emits an X-ray beam from a number of different positions (angles). An examination subject 2 is arranged in the beam path of a beam bundle emitted by the beam transmitter 1, with a region 3, schematically shown for exemplary purposes as a sphere, of the examination subject 2 forms a reference object 4. The region 3 can for example be fastened temporarily on the examination subject 2 by means of adhesive. The beam shadow of the examination subject 2 and that of the region 3 strike a beam receiver 5, whose output signals are supplied to an image generation unit 6 in order to produce a tomosynthesis image of the examination subject 2. The reference object 4 can also be a tooth filling, a crown, an implant or a metal part, located on or in or at least in the vicinity of the examination subject 2. The reference object 4 is preferably arranged immediately on the subject of examination 2.

Figure 2:
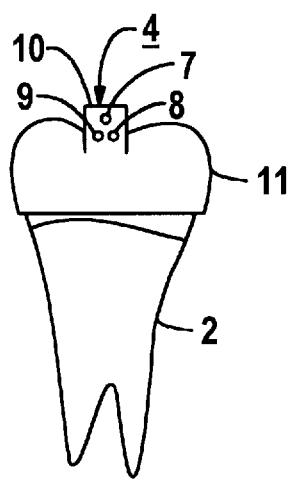
FIG. 2 shows a reference object that is connected with the examination subject via a mounting constructed as a cap for implementing the inventive method.

In the exemplary embodiment according to FIG. 2, the reference object is formed by at least two, preferably three, sub-objects 7, 8 and 9, arranged on a tongue 10 of a cap 11. The cap 11 is placed over the examination subject 2, which is, for example, a tooth. The sub-objects 7, 8 and 9 preferably consist of a material that differs as strongly as possible from that of the examination subject 2 with respect to absorption of radiation. For this purpose, the sub-objects 7, 8 and 9 preferably consist of metal, or can be fashioned as holes in a tongue 10 made of metal. The cap 11 is preferably manufactured from a material that is substantially transparent to radiation, so that it causes no disturbance during the X-ray exposure.

Figure 3:
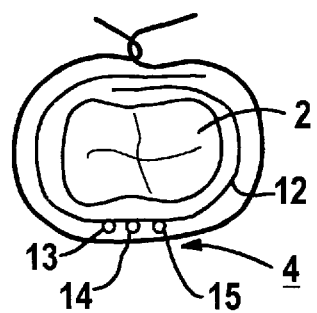
FIG. 3 shows a mounting constructed as a ring for implementing the inventive method.

In the embodiment shown in FIG. 3, the reference object 4 is formed by a ring 12 that includes sub-objects 13, 14 and 15, which are likewise distinguished from the examination subject 2 with respect to radiation absorption. The ring 12 hereby likewise preferably consists of a material that appears as faintly as possible in the produced Xray exposure. Of course, instead of a cap 11 or a ring 12, but also any other suitable mounting means can be used within the scope of the invention. In particular, the angle of irradiation and the distance of the examination subject 2 to the beam receiver 5 can be determined precisely on the basis of the known size of the arrangement and/or the distances of the sub-objects 7, 8 and 9, or 13, 14 and 15 to one another.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for producing a tomosynthesis exposure of a tooth comprising the steps of:

forming a reference object from a tooth filling of a tooth;

irradiating said tooth including said reference object with X-rays from a plurality of different directions;

detecting X-rays attenuated by said tooth and by said reference object from each of said different directions and thereby producing a set of detection signals; and generating a tomosynthesis exposure of said tooth from said set of detection signals.

2. An X-ray diagnostic apparatus for dental tomosynthesis comprising:

a radiation emitter which emits an X-ray beam and means for emitting said X-ray beam toward a tooth from a plurality of different angles;

a reference object and a cap fittable over said tooth for attaching said reference object directly to said tooth;

a radiation receiver which is struck by said X-ray beam from said plurality of different angles, attenuated by said reference object and said tooth, and which emits electrical signals corresponding to X-rays incident thereon; and means for generating a tomosynthesis image of said tooth from said electrical signals.

3. A method for producing a tomosynthesis exposure of a tooth comprising the steps of:

forming a reference object from a crown on a tooth;

irradiating said tooth including said reference object with X-rays from a plurality of different directions;

detecting X-rays attenuated by said tooth and by said reference object from each of said different directions and thereby producing a set of detection signals; and generating a tomosynthesis exposure of said tooth from said set of detection signals.

4. A method for producing a tomosynthesis exposure of a tooth comprising the steps of:

forming a reference object from a dental implant on a tooth;

irradiating said tooth including said reference object with X-rays from a plurality of different directions;

detecting X-rays attenuated by said tooth and by said reference object from each of said different directions and thereby producing a set of detection signals; and generating a tomosynthesis exposure of said tooth from said set of detection signals.

5. A method for producing a tomosynthesis exposure of a tooth comprising the steps of:

forming a reference object from a metal part attached to a tooth;

irradiating said tooth including said reference object with X-rays from a plurality of different directions;

detecting X-rays attenuated by said tooth and by said reference object from each of said different directions and thereby producing a set of detection signals; and generating a tomosynthesis exposure of said tooth from said set of detection signals.

6. A method for producing a tomosynthesis exposure of a tooth comprising the steps of:

temporarily attaching a reference object to a tooth by adhesive;

irradiating said tooth including said reference object with X-rays from a plurality of different directions;

detecting X-rays attenuated by said tooth and by said reference object from each of said different directions and thereby producing a set of detection signals; and generating a tomosynthesis exposure of said tooth from said set of detection signals.

7. A method for producing a tomosynthesis exposure of a tooth comprising the steps of:

attaching a reference object to a tooth by a mount fitted on said tooth formed by a cap covering a portion of said tooth;

irradiating said tooth including said reference object with X-rays from a plurality of different directions;

detecting X-rays attenuated by said tooth and by said reference object from each of said different directions and thereby producing a set of detection signals; and generating a tomosynthesis exposure of said tooth from said set of detection signals.

8. A method for producing a tomosynthesis exposure of a tooth comprising the steps of:

attaching a reference object to a tooth by a mount fitted on said tooth formed by a ring surrounding said tooth;

irradiating said tooth including said reference object with X-rays from a plurality of different directions;

detecting X-rays attenuated by said tooth and by said reference object from each of said different directions and thereby producing a set of detection signals; and generating a tomosynthesis exposure of said tooth from said set of detection signals.

9. An X-ray diagnostic apparatus for dental tomosynthesis comprising:

a radiation emitter which emits an X-ray beam and means for emitting said X-ray beam toward a tooth from a plurality of different angles;

a reference object and a ring surrounding said tooth for attaching said reference object directly to said tooth;

a radiation receiver which is struck by said X-ray beam from said plurality of different angles, attenuated by said reference object and said tooth, and which emits electrical signals corresponding to X-rays incident thereon; and means for generating a tomosynthesis image of said tooth from said electrical signals.

10. An X-ray diagnostic apparatus for dental tomosynthesis comprising:

a radiation emitter which emits an X-ray beam and means for emitting said X-ray beam toward a tooth from a plurality of different angles;

a metallic reference object adhesively attached to said tooth;

a radiation receiver which is struck by said X-ray beam from said plurality of different angles, attenuated by said reference object and said tooth, and which emits electrical signals corresponding to X-rays incident thereon; and means for generating a tomosynthesis image of said tooth from said electrical signals.

* * * * *